United States Patent [19]

Ingle et al.

[11] 4,206,203

[45] Jun. 3, 1980

[54] METHOD FOR TREATING KETOTIC RUMINANTS WITH ANTIBIOTIC AV290

[75] Inventors: Donald L. Ingle, Trenton; Ronald H. Dalrymple, Titusville, both of N.J.

[73] Assignee: American Cyanamid Company, Stamford, Conn.

[21] Appl. No.: 952,033

[22] Filed: Oct. 16, 1978

Related U.S. Application Data

[62] Division of Ser. No. 799,822, May 23, 1977.

[51] Int. Cl.$^2$ ............................................. A61K 35/66
[52] U.S. Cl. .................................................... 424/118
[58] Field of Search ......................................... 424/118

*Primary Examiner*—Sam Rosen

*Attorney, Agent, or Firm*—H. G. Jackson

[57] ABSTRACT

This invention relates to a method for improving the production of propionic acid and thus increasing the propionate:acetate ratio in the course of the microbiological conversion of cellulose and starch containing feedstuffs to short chain volatile fatty acids in the ruminant animal. This invention further relates to the use of antibiotic AV290, antibiotic AV290 sulfate, an antibiotic AV290-syntan complex, an antibiotic AV290-alkyl sulfate complex, and/or an antibiotic AV290 alkylated derivative for increasing the production of propionic acid and suppressing the production of acetic acid during the microbiological digestive processes taking place in the animal rumen and treating ketosis.

4 Claims, No Drawings

METHOD FOR TREATING KETOTIC RUMINANTS WITH ANTIBIOTIC AV290

This is a division of application Ser. No. 799,822 filed May 23, 1977.

BACKGROUND OF THE INVENTION

The major nutritive portion of the ruminants diet consists primarily of polysaccharides such as cellulose and starches. These primary sources of said animals energy requirements, and of basic intermediates for tissue building processes, are hydrolized in said animals rumen by microbiological processes to monosaccharides, primarily to glucose. The thus formed glucose is then further degraded by enzymatic processes to pyruvic acid and derivatives thereof. These in turn are further converted through various enzymatic processes to acetic acid and propionic acid and derivatives thereof. Simultaneously, and also in the rumen, some of the acetic acid is converted to butyric acid. Although butyric acid is the component most efficiently metabolized by ruminants while acetic acid is the least efficiently utilized product of the above referred-to digestive processes, the formation of butyric acid in the course of said microbiological processes is energetically not very favorable. As stated above, butyric acid is formed from acetic acid, and since one mole of glucose yields two moles of acetic acid and two moles of methane and/or carbon dioxide gas, and since two moles of acetic acid are consumed in the formation of one mole of butyric acid, therefore, for every mole of butyric acid formed, two moles of methane and/or carbon dioxide gas are generated, representing a considerable energy loss. Additionally, it is known that production of acetic acid (and/or acetates) in larger than normal amounts may lead to the production of ketone bodies (acetoacetate, acetone and $\beta$-hydroxy butyrate) which can cause ketosis in ruminants, especially if said animals are under stress. It has been found that the supplementary feeding of propionic acid (and/or propionates) is beneficial for minimizing the effects of ketosis. A further advantage of feeding a diet high in propionic acid to ruminants such as cattle, sheep and goats is to lower the incidence of ketosis.

Thus it would be of advantage both to the animal grower and feedlot operator if the microbiological processes of the rumen could be altered so that the production of propionic acid from carbohydrates is enhanced while that of acetic acid is suppressed.

BRIEF SUMMARY OF THE INVENTION

This invention relates to novel compositions of matter useful in favorably altering the acetate:propionate ratio in the course of the microbiological digestive processes taking place in the rumen of animals such as cattle, sheep and goats. More particularly, it relates to compositions containing one or more of the following active ingredients (in any proportions) which are useful for enhancing the production of propionates in said animals rumen while the animals feed is digested:

(1) antibiotic AV290 whose preparation and properties are disclosed in U.S. Pat. No. 3,338,786;

(2) antibiotic AV290 sulfate which is disclosed in U.S. Pat. No. 3,855,410.

(3) an antibiotic AV290-syntan complex prepared as described in U.S. Pat. No. 3,832,462;

(4) an antibiotic AV290-alkyl sulfate complex derived by treatment of the antibiotic with an alkali metal alkyl sulfate as set forth in U.S. Pat. No. 3,856,937;

(5) an antibiotic AV290 alkylated derivative derived by treatment of the antibiotic with a lower alkyl halide as defined and described in U.S. Pat. No. 3,954,973.

The invention includes not only the new compositions of matter but also the methods of enhancing the production of propionates while simultaneously suppressing the production of acetates and thereby minimizing the incidence of ketosis in said ruminants.

DETAILED DESCRIPTION OF THE INVENTION

The present invention is based upon the discovery that although the above-described active ingredients have been utilized for promoting the growth rate of poultry and farm animals, the effect of said compounds in favorably altering the acetate:propionate ratio during the microbiological processes taking place in the rumen have been hitherto unknown and not predictable from knowledge of the prior use and activity of said compounds. The novel method of the present invention comprises orally administering to ruminants such as cattle, sheep and goats antibiotic AV290 or the above-identified salts, complexes, and derivatives thereof in amounts sufficient to promote the formation of propionates while suppressing the formation of acetates.

Advantageously, we have found that by orally administering to said ruminants antibiotic AV290 or the above-identified salts, complexes, or derivatives thereof (and/or mixtures thereof) in amounts of from about 10 mg. to about one gram per head per day from about 0.05 mg. to about 50.0 mg./kg. of body weight per day, the acetate:propionate ratio is altered in favor of the propionates in the course of the microbiological digestive processes taking place in the rumen of said animals. Thus, by promoting the formation of propionates and suppressing the formation of acetates, the incidence of ketosis among said ruminants is minimized.

The active compounds of this invention, antibiotic AV290 and the salts, complexes, and derivatives thereof, can be conveniently administered to cattle, sheep and goats as feed additives in amounts ranging from about 8 grams to about one kilogram per ton of feed to provide 10 mg. to one gram per head per day or 0.05 mg. to 50.0 mg./kg. of body weight per day of said compound. Should it be desired, antibiotic AV290 and its pharmaceutically acceptable salts, complexes, and derivatives may also be formulated for oral administration as feed premixes, concentrates, tablets, pills and boluses, which may be prepared by accepted and well known methods, using pharmaceutically acceptable carriers, diluents, binding and lubricating agents.

The present invention is further illustrated by the non-limiting examples set forth below:

EXAMPLE 1

Evaluation of the in vitro efficacy of the antibiotic AV290 for altering the acetic acid:propionic acid ration during fermentation in rumen fluid The steers used in the experiment have surgically installed fistulas that open into the rumen. The steers are offered water and a daily ration of alfalfa hay ad libitum as well as 10 lbs. of a standard 15% protein grain ration of the following composition:

| Component | Percent by Weight |
| --- | --- |
| Corn | 32.7 |
| Barley | 10.0 |
| Oats | 7.5 |
| Molasses | 10.0 |
| Soybean Oil Meal (48% protein) | 13.8 |
| Beet Pulp | 2.5 |
| Corn Gluten Feed | 12.5 |
| Distillers Grain | 7.5 |
| Trace Mineral Mix | 0.05 |
| Salt | 1.0 |
| Dicalcium Phosphate | 2.0 |

Method

A sample of rumen fluid (500 ml.) is aspirated into a flask and strained through four layers of cheesecloth to remove coarse feed particles. Ten ml. of the clarified centrifuged at 2,000×g for 15 minutes and the clear supernatant removed for analysis by gas chromatography to determine concentrations of acetic and propionic acid, and butyric acid in the samples. The data obtained are summarized in Table I and show the molar percent of each volatile fatty acid (VFA) produced during fermentation in the presence of antibiotic AV290 as well as the ratio, acetic to propionic acid; while in Table II the same data are expressed as percent change from the control.

Table I

| Treatment | Level of Drug in Substrate; ppm | Molar Percent of VFA | | | Ratio Acetic/propionic |
| --- | --- | --- | --- | --- | --- |
| | | Acetic | Propionic | Butyric | |
| Control | 0 | 58.9 | 24.4 | 16.7 | 2.41 |
| AV 290 Sulfate | 5,000 | 53.9 | 29.8 | 16.3 | 1.81 |
| | 1,000 | 55.2 | 33.2 | 11.5 | 1.66 |
| | 200 | 56.4 | 29.4 | 14.2 | 1.92 |
| | 100 | 56.0 | 30.6 | 13.4 | 1.83 |
| | 40 | 56.6 | 25.3 | 18.1 | 2.24 |
| AV 290 Lauryl Sulfate | 5,000 | 55.2 | 31.4 | 13.4 | 1.76 |
| | 1,000 | 55.3 | 31.1 | 13.6 | 1.78 |
| | 200 | 56.8 | 30.3 | 13.8 | 1.87 |
| | 40 | 57.1 | 24.8 | 18.1 | 2.30 |

Table II

| Treatment | Level of Drug in Substrate; ppm | Percent Change from Control | | | Percent Change From Control:Ratio Acetic/Propionic |
| --- | --- | --- | --- | --- | --- |
| | | Acetic | Propionic | Butyric | |
| AV 290 Sulfate | 5,000 | −8.5 | +22.1 | −2.4 | −24.9 |
| | 1,000 | −6.3 | +36.1 | −31.1 | −31.1 |
| | 200 | −4.2 | +20.5 | −15.0 | −20.3 |
| | 40 | −3.9 | +3.6 | +8.4 | −7.1 |
| AV 290 Lauryl Sulfate | 5,000 | −6.3 | +28.7 | −19.8 | −27.0 |
| | 1,000 | −6.1 | +27.5 | −18.6 | −26.1 |
| | 200 | −3.6 | +24.2 | −22.2 | −22.4 |
| | 40 | −3.1 | +1.6 | +8.4 | −4.6 |

The above data clearly show that antibiotic AV290 preparations are effective in increasing the propionic acid production while simultaneously suppressing acetic acid production during fermentation in rumen fluid.

EXAMPLE 2

Evaluation of the in vivo efficacy of antibiotic AV290 for altering the acetic acid:propionic acid ratio during fermentation in the rumen of sheep Twenty-four whether lambs, weighing approximately 40 kg. each, are randomly allotted to four groups of 6 lambs each. One group serves as unmedicated control and receives water and the following diet ad libitum:

| Component | Percent by Weight |
| --- | --- |
| Ground corn cob | 35.0 |
| Dehydrated alfalfa meal | 20.0 |
| Ground corn | 19.4 |
| Cane molasses | 12.0 |
| Soybean oil meal (48% protein) | 12.0 |
| Dicalcium phosphate | 1.0 |
| Iodized salt | 0.5 |
| Trace mineral mix | 0.1 |
| Vitamin A and D₃ premix | 0.02 |
| Corn oil | 0.01 |

The other three groups receive water and the same diet ad libitum, except that 20, 50 or 100 ppm. of AV290 lauryl sulfate is incorporated into the diet of the respective groups. After 19 days on the diet, the sheep are sacrificed and samples of rumen fluid are obtained and analyzed as in Example 1. The data obtained are summarized in Table III and show the molar percent of each volatile fatty acid (VFA) produced in the presence of AV290 as well as the ratio of acetic to propionic acid; while in Table IV the same data are expressed as percent change from the control.

Table III

| Treatment | Level of Drug in Feed; ppm | VFA Molar Percent | | | Ratio of Acetic/propionic |
| --- | --- | --- | --- | --- | --- |
| | | Acetic | Propionic | Butyric | |
| Control | 0 | 69.1 | 15.7 | 15.2 | 4.40 |
| AV 290 Lauryl Sulfate | 20 | 64.8 | 22.7 | 12.5 | 2.85 |
| | 50 | 62.7 | 26.9 | 10.4 | 2.33 |
| | 100 | 58.1 | 32.0 | 9.9 | 1.82 |

Table IV

| Treatment | Level of Drug in Feed; ppm | Percent Change from Control | | | Ratio Acetic/propionic |
| --- | --- | --- | --- | --- | --- |
| | | Acetic | Propionic | Butyric | |
| AV 290 Lauryl Sulfate | 20 | −6.2 | +44.2 | −17.8 | −35.2 |
| | 50 | −9.3 | +71.3 | −31.6 | −47.0 |
| | 100 | −15.9 | +103.8 | −34.9 | −58.6 |

The above data, especially those found in Table IV, clearly show that AV290 lauryl sulfate is very effective in increasing the propionic acid production while suppressing the acetic acid production in vivo, when orally administered to sheep.

EXAMPLE 3

Evaluation of the efficacy of AV290 for altering the acetic acid:propionic acid ratio during fermentation in the rumen of cattle Eighteen feedlot cattle, weighing approximately b 350 kg. each, are randomly allotted to three groups of 6 animals each. Water and the ration described in Example 2 are offered to the animals ad libitum. One group serves as unmedicated control, while groups two and three each receive in their daily diet 33 ppm. or 99 ppm. of AV290 lauryl sulfate, respectively.

The feeding trial is conducted for a period of 56 days, with rumen fluid samples being obtained from the animals on days 14, 28 and 56 after the beginning of the trial. The rumen fluid samples are handled and analyzed for volatile fatty acids (VFA) by the method of Example 1. The thus obtained data are summarized in Table V, while in Table VI the same data are expressed as percent change from the controls.

It can be clearly seen from Table V and especially from Table VI that the oral administration of AV290 lauryl sulfate to cattle via their diet very effectively alters the VFA production during fermentation in the rumen of said animals in favor of propionic acid.

We claim:

1. A method of treating ketotic ruminants which comprises administering to said ruminants an oral ration containing a pharmaceutically effective amount of an active ingredient selected from the group consisting of antibiotic AV290, antibiotic AV290 sulfate, an antibiotic AV290-alkyl sulfate complex, an antibiotic AV290 alkylated derivative and mixtures thereof in any proportion.

2. The method according to claim 1 wherein the ruminants are cattle.

3. The method according to claim 1 wherein the ruminants are sheep.

4. The method according to claim 1 wherein the ruminants are goats.

Table V

| Treatment | Level of Drug in Feed; ppm | Date/Days from Start | VFA Molar Percent | | | Ratio of Acetic/ propionic |
|---|---|---|---|---|---|---|
| | | | Acetic | Propionic | Butyric | |
| Control | 0 | 14 | 69.2 | 17.4 | 13.4 | 3.98 |
| | | 28 | 69.6 | 18.6 | 11.8 | 3.74 |
| | | 56 | 65.8 | 19.4 | 14.8 | 3.39 |
| AV 290 Lauryl Sulfate | 33 | 14 | 65.7 | 22.0 | 12.3 | 2.98 |
| | | 28 | 64.8 | 22.5 | 12.7 | 2.88 |
| | | 56 | 61.5 | 23.2 | 15.2 | 2.65 |
| | 99 | 14 | 61.9 | 28.2 | 9.9 | 2.20 |
| | | 28 | 60.1 | 28.9 | 11.1 | 2.08 |
| | | 56 | 58.8 | 28.3 | 12.9 | 2.08 |

Table VI

| Treatment | Level of Drug in Feed; ppm | Date/Days from Start | Percent Change from Controls | | | Ratio: Acetic/ propionic |
|---|---|---|---|---|---|---|
| | | | Acetic | Propionic | Butyric | |
| AV 290 Lauryl Sulfate | 33 | 14 | −5.1 | +26.4 | −8.2 | −24.9 |
| | | 28 | −6.9 | +21.0 | +7.6 | −23.0 |
| | | 56 | −4.3 | +19.6 | +2.7 | −21.8 |
| | 99 | 14 | −10.5 | +62.1 | +26.1 | −44.7 |
| | | 28 | −13.5 | +55.4 | +5.9 | −44.4 |
| | | 56 | −10.6 | +45.9 | +12.8 | −38.6 |